US011236027B2

(12) United States Patent
Elia et al.

(10) Patent No.: US 11,236,027 B2
(45) Date of Patent: Feb. 1, 2022

(54) HEAVY AROMATICS CONVERSION PROCESSES AND CATALYST COMPOSITIONS USED THEREIN

(71) Applicant: ExxonMobil Chemical Patents Inc., Baytown, TX (US)

(72) Inventors: Christine N. Elia, Bridgewater, NJ (US); Wenyih F. Lai, Bridgewater, NJ (US); Hari Nair, Spring, TX (US); Joshua I. Cutler, Houston, TX (US); Chuansheng Bai, Phillipsburg, NJ (US); Nicholas S. Rollman, Hamburg, PA (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 17/201,803

(22) Filed: Mar. 15, 2021

(65) Prior Publication Data

US 2021/0198165 A1 Jul. 1, 2021

Related U.S. Application Data

(62) Division of application No. 16/337,271, filed as application No. PCT/US2017/053889 on Sep. 28, 2017, now Pat. No. 10,981,845.

(Continued)

(30) Foreign Application Priority Data

Nov. 30, 2016 (EP) .................................... 16201374

(51) Int. Cl.
*B01J 29/26* (2006.01)
*C07C 4/18* (2006.01)
*B01J 29/48* (2006.01)
*B01J 29/78* (2006.01)
*B01J 29/80* (2006.01)
*B01J 35/02* (2006.01)
*B01J 37/20* (2006.01)
(Continued)

(52) U.S. Cl.
CPC ................. *C07C 4/18* (2013.01); *B01J 29/26* (2013.01); *B01J 29/48* (2013.01); *B01J 29/7869* (2013.01); *B01J 29/7876* (2013.01); *B01J 29/80* (2013.01); *B01J 35/023* (2013.01); *B01J 37/20* (2013.01); *C07C 6/126* (2013.01); *C10G 35/095* (2013.01); *B01J 2229/186* (2013.01); *B01J 2229/20* (2013.01); *B01J 2229/36* (2013.01); *B01J 2229/40* (2013.01); *C07C 2529/18* (2013.01); *C07C 2529/40* (2013.01); *C07C 2529/70* (2013.01); *C07C 2529/78* (2013.01); *C07C 2529/80* (2013.01); *C10G 2300/1096* (2013.01); *C10G 2300/30* (2013.01); *C10G 2300/70* (2013.01); *C10G 2400/30* (2013.01)

(58) Field of Classification Search
CPC ..... C07C 4/18; C07C 6/126; C07C 2529/068; C07C 2529/072; C07C 2529/12; C07C 2529/16; C07C 2529/18; C07C 2529/24; C07C 2529/40; C07C 2529/44; C07C 2529/48; C07C 2529/70; C07C 2529/78; C07C 2529/80; C07C 2529/076; C07C 2529/14; C07C 2529/22; C07C 2529/26; C07C 2529/46; C07C 2529/74; C07C 15/04; C07C 15/06; C07C 15/08; C10G 35/095; C10G 2400/30; C10G 2300/1096; C10G 2300/30; C10G 2300/70; B01J 37/20; B01J 35/023; B01J 35/026; B01J 35/1061; B01J 2229/186; B01J 2229/20; B01J 2229/36; B01J 2229/40; B01J 2229/42; B01J 29/068; B01J 29/072; B01J 29/076; B01J 29/12; B01J 29/126; B01J 29/14; B01J 29/146; B01J 29/22; B01J 29/24; B01J 29/26; B01J 29/44; B01J 29/46; B01J 29/48; B01J 29/7415; B01J 29/7423; B01J 29/7438; B01J 29/7446; B01J 29/7453; B01J 29/7461; B01J 29/7469; B01J 29/7476; B01J 29/7484; B01J 29/7492; B01J 29/7615; B01J 29/7623; B01J 29/7638; B01J 29/7646; B01J 29/7653; B01J 29/7669; B01J 29/7676; B01J 29/7684; B01J 29/7661; B01J 29/7692; B01J 29/7815; B01J 29/7823; B01J 29/7838; B01J 29/7846; B01J 29/7853; B01J 29/7861; B01J 29/7884; B01J 29/7892; B01J 29/7869; B01J 29/7876; B01J 29/80; B01J 29/90; B01J 2029/081
See application file for complete search history.

(56) References Cited

U.S. PATENT DOCUMENTS

| 5,763,720 A | 6/1998 | Buchanan et al. ............. 585/475 |
| 5,942,651 A | 8/1999 | Beech, Jr. et al. ............. 585/475 |

(Continued)

FOREIGN PATENT DOCUMENTS

| KR | 2016/0036136 | 9/2014 | ............ B01J 29/061 |
| WO | 2013/127044 | 6/2013 | ............ B01J 29/146 |

*Primary Examiner* — Youngsul Jeong
*Assistant Examiner* — Jason Y Chong

(57) ABSTRACT

Disclosed are processes for conversion of a feedstock comprising $C_{8+}$ aromatic hydrocarbons to lighter aromatic products in which the feedstock and optionally hydrogen are contacted in the presence of the catalyst composition under conversion conditions effective to dealkylate and transalkylate said $C_{8+}$ aromatic hydrocarbons to produce said lighter aromatic products comprising benzene, toluene and xylene. The catalyst composition comprises a zeolite, a first metal, and a second metal, and is treated with a source of sulfur and/or a source of steam.

3 Claims, No Drawings

Related U.S. Application Data

(60) Provisional application No. 62/406,155, filed on Oct. 10, 2016.

(51) Int. Cl.
  *C07C 6/12* (2006.01)
  *C10G 35/095* (2006.01)

(56) References Cited

U.S. PATENT DOCUMENTS

| | | |
|---|---|---|
| 6,867,340 B2 | 3/2005 | Oh et al. .................. 585/475 |
| 7,109,389 B2 | 9/2006 | Kong et al. ............... 585/302 |
| 7,148,391 B1 | 12/2006 | Buchanan et al. ........ 585/475 |
| 7,687,423 B2 | 3/2010 | Moscoso et al. ........... 502/60 |
| 8,183,424 B2 | 5/2012 | Levin et al. .............. 585/323 |
| 8,481,795 B2 | 7/2013 | Boldingh et al. .......... 585/475 |
| 9,006,125 B2 | 5/2015 | Levin et al. .............. B01J 8/04 |
| 10,118,165 B2 | 11/2018 | Lai et al. ................ B01J 29/80 |
| 2002/0091060 A1 | 7/2002 | Cheng et al. .............. 502/63 |
| 2011/0190556 A1 | 8/2011 | Levin et al. .............. 585/251 |
| 2012/0083635 A1 | 4/2012 | Boldingh et al. ........ 585/375 |
| 2012/0277512 A1 | 11/2012 | Boldingh ................. 585/486 |
| 2015/0353447 A1 | 12/2015 | Abichandani et al. ... C07C 4/18 |
| 2016/0220987 A1 | 8/2016 | Lai et al. ............... B01J 29/80 |

# HEAVY AROMATICS CONVERSION PROCESSES AND CATALYST COMPOSITIONS USED THEREIN

CROSS-REFERENCE TO RELATED APPLICATIONS

This application is a Divisional Application of U.S. Ser. No. 16/337,271, filed Mar. 27, 2019, which is the National Phase Application of PCT Application Serial No. PCT/US2017/053889, filed Sep. 28, 2017, which claims the benefits of and priorities to U.S. Provisional Application Ser. No. 62/406,155, filed Oct. 10, 2016, and European Application No. 16201374.2, filed Nov. 30, 2016, the disclosures of which are incorporated herein by reference in their entireties.

FIELD

The invention relates to a process for conversion of heavy aromatics, specifically $C_{8+}$ aromatic hydrocarbons, to lighter aromatic products, particularly benzene, toluene and xylenes (hereinafter collectively referred to as BTX), and a catalyst composition for use in such process. More specifically, the invention relates to a process for the production of xylenes in the presence of a catalyst composition comprising a zeolite, a first metal and, optionally, a second metal.

BACKGROUND

The transalkylation of low value $C_{9+}$ aromatics with benzene or toluene to produce xylenes is an increasingly important process. Chemical plants would ideally like to process as much of the heavy $C_{9+}$ aromatics as possible while minimizing and potentially removing the toluene/benzene co-feed. Both transalkylation activity and dealkylation activity are important for a successful catalyst system. Transalkylation is the ability to transalkylate methyl groups to form xylenes. Dealkylation activity is the ability to dealkylate ethyl and propyl groups present on the $C_{9+}$ aromatics to allow the formation of lower methyl/ring species that may undergo transalkylation with higher methyl/ring species to form xylenes. Metal function is required to saturate olefins formed during dealkylation. As chemical plants move to increased amounts of $C_{9+}$ in the feed, acceptable activity and catalyst life become challenging.

The need exists for an improved process for conversion of a feedstock comprising $C_{8+}$ aromatic hydrocarbons to lighter aromatic products, such as xylene.

SUMMARY

It has now been found that a catalyst composition of this invention is effective at saturating the olefins produced in a heavy aromatics conversion process while minimizing the saturation of the desired lighter aromatic products, including, but not limited to the xylene isomers, when said catalyst composition is treated with a source of sulfur and/or a source of steam.

In a first aspect, the invention relates to a process for conversion of a feedstock comprising $C_{8+}$ aromatic hydrocarbons to lighter aromatic products. The feedstock and optionally hydrogen are contacted in the presence of a catalyst composition under conversion conditions effective to dealkylate and transalkylate said $C_{8+}$ aromatic hydrocarbons to produce said lighter aromatic products comprising benzene, toluene and xylene. The catalyst composition is treated with a source of sulfur and/or a source of steam. Typically, the $C_{8+}$ aromatic hydrocarbons in the feedstock comprises aromatic compounds having a boiling point in the range of 135° C. to 230° C. at atmospheric pressure. Typically, the feedstock further comprises benzene or toluene or a mixture thereof. In further embodiments, the catalyst composition is treated with a source of sulfur and optionally with a source of steam.

Preferably, the treatment with a source of sulfur is in one or more steps at temperatures in the range 204° C. (400° F.) up to about 480° C. (900° F.).

The source of sulfur is one or more of hydrogen sulfide, carbon disulfide and alkylsulfides which are selected from the group consisting of methylsulfide, dimethylsulfide, dimethyldisulfide, diethylsulfide and dibutyl sulfide, and mixtures of two or more thereof.

Preferably, the treatment with a source of steam may be up to about 100% steam at temperatures in the range of about 260° C. (500° F.) to about 649° C. (1200° F.) and said treatment is in one or more temperature steps.

In one or more embodiments, the zeolite has a constraint index of less than 12; or in the range of 3 to 12, or in the range of 5 to 9, or in the range of 0.6 to 3, or in the range of 0.3 to 0.6.

In one or more embodiments, the catalyst composition comprises: (i) at least one zeolite, (ii) 0.001 wt. % to 20.0 wt. % of at least one first metal, said first metal being in Group 6 of the Periodic Table, based on the weight of said catalyst composition, and (iii) 0.001 wt. % to 20.0 wt. % of at least one second metal, said second metal being in Group 9 or Group 10 of the Periodic Table, based on the weight of said catalyst composition.

Preferably, the first metal is molybdenum or tungsten or a mixture thereof. Preferably, the second metal is cobalt or nickel.

In a second aspect, the invention relates to a process for conversion of a feedstock comprising $C_{8+}$ aromatic hydrocarbons in which the feedstock and optionally hydrogen are contacted in the presence of a treated catalyst composition under conversion conditions effective to dealkylate and transalkylate said $C_{8+}$ aromatic hydrocarbons to produce lighter aromatic products comprising benzene, toluene and xylene. The treated catalyst composition is made by a method comprising the steps of providing a catalyst composition that comprises at least one zeolite, and contacting said catalyst composition with a source of a first metal or compounds thereof and a source of a different second metal or compounds thereof to form a metal-containing catalyst composition. The identity and amounts of the first metal and the second metal are as described above. The metal-containing catalyst composition is treated with a source of sulfur and/or a source of steam to form the treated catalyst composition, as set forth above.

In a third aspect, the invention relates to a catalyst composition which comprises (i) a zeolite, (ii) 0.001 wt. % to 20.0 wt. % of at least one first metal, and (iii) 0.001 wt. % to 20.0 wt. % of at least one second metal, each wt. % based on the weight of the catalyst composition, wherein the catalyst composition is treated with a source of sulfur, preferably, in one or more steps at temperatures in the range 204° C. (400° F.) up to about 480° C. (900° F.) or treated with a source of steam, preferably, which comprises up to about 100% steam at temperatures in the range of about 260° C. (500° F.) to about 649° C. (1200° F.).

The zeolite may be selected from the group consisting of zeolite beta, ZSM-4, ZSM-5, ZSM-11, ZSM-12, ZSM-20, ZSM-22, ZSM-23, ZSM-35, ZSM-48, ZSM-50, ZSM-57, ZSM-58, MCM-68, a faujasite zeolite, a mordenite zeolite, a MCM-22 family material, or a mixture thereof. In one or more embodiments, the zeolite comprises zeolite beta, ZSM-5, ZSM-12 or a mordenite zeolite which is synthesized from TEA or MTEA, as defined herein. In one or more embodiments, the first metal comprises molybdenum or tungsten, or a mixture thereof. In one or more embodiments, the second metal comprises cobalt or nickel, or a mixture thereof. In further embodiments, the first metal is molybdenum and the second metal is cobalt or the first metal is tungsten and the second metal is nickel.

DETAILED DESCRIPTION OF TILE EMBODIMENTS

Definitions

For the purpose of this specification and appended claims, the following terms are defined.

As used herein, the term "$C_n$ aromatic hydrocarbon" means an aromatic hydrocarbon having n carbon atom(s) per molecule, wherein n is a positive integer. The term "$C_{n+}$ aromatic hydrocarbon" means an aromatic hydrocarbon having at least n carbon atom(s) per molecule. The term "$C_{n-}$ aromatic hydrocarbon" means an aromatic hydrocarbon having no more than n carbon atom(s) per molecule.

As used herein, the term "aromatic" means substituted and unsubstituted mono- and poly-nuclear ring compounds. Compounds of the benzene series as well as compounds of an aromatic character which are or contain a heterocyclic ring are examples of aromatic compounds. These substituted aromatic compounds must, however, contain at least 1 hydrogen attached to the aromatic nucleus. The aromatic rings may be substituted with alkyl groups, aryl groups, alkaryl groups, hydroxy groups, amine groups, alkoxy groups, aryloxy groups, cycloalkyl groups, halide groups, and mixtures of these groups and other radicals which do not prevent the desired reaction.

The term "hydrocarbon" means a class of compounds containing hydrogen bound to carbon, and encompasses (i) saturated hydrocarbon compounds, (ii) unsaturated hydrocarbon compounds, and (iii) mixtures of hydrocarbon compounds (saturated and/or unsaturated), including mixtures of hydrocarbon compounds having different values of n.

As used herein, the term "lighter aromatic products" is defined to mean that the aromatic molecules in the products have fewer carbon atoms than the carbon atoms of the aromatic molecules in the feedstock. For example, para-xylene, one of the resulting products of $C_{9+}$ transalkylation with toluene and/or benzene, has 8 carbon atoms which is less than 9 or more carbon atoms in $C_{9+}$ aromatic molecules.

As used herein, the term "Periodic Table" means the Periodic Table of the Elements of the International Union of Pure and Applied Chemistry, dated 1 May 2013, as it appears on the inside cover of The Merck Index, Twelfth Edition, Merck & Co., Inc., 1996.

As used herein, the term "meso-mordenite" means a mordenite zeolite synthesized from TEA or MTEA, having a mesopore surface area of greater than 30 m²/g and said mordenite zeolite comprising agglomerates composed of primary crystallites, wherein said primary crystallites have an average primary crystal size as measured by TEM of less than 80 nm and an aspect ratio of less than 2, as disclosed in U.S. Publication No. 2016-0221832, incorporated by reference in its entirety.

As used herein, the term "constraint index" is defined in U.S. Pat. Nos. 3,972,832 and 4,016,218, both of which are incorporated herein by reference. A determination of the "constraint index" may be made of by passing continuously a mixture of an equal weight of normal hexane and 3-methylpentane over a small sample, approximately 1 gram or less, of catalyst at atmospheric pressure according to the following procedure. A sample of the catalyst, in the form of pellets or extrudate, is crushed to a particle size about that of coarse sand and mounted in a glass tube. Prior to testing, the catalyst is treated with a stream of air at 538° C. (1000° F.) for at least 15 minutes. The catalyst is then flushed with helium and the temperature adjusted between 288° C. (550° F.) and 510° C. (950° F.) to give an overall conversion between 10% and 60%. The mixture of hydrocarbons is passed at 1 liquid hourly spaced velocity (i.e., 1 volume of liquid hydrocarbon per volume of catalyst per hour) over the catalyst with a helium dilution to give a helium to total hydrocarbon mole ratio of 4:1. After 20 minutes on stream, a sample of the effluent is taken and analyzed, most conveniently by gas chromatography, to determine the fraction remaining unchanged fix each of the two hydrocarbons. The "constraint index" approximates the ratio of the cracking rate constants for the two hydrocarbons and is calculated as follows:

$$\text{constraint index} = \frac{\log_{10}(\text{fraction of } n\text{-hexane remaining})}{\log_{10}(\text{fraction of 3-methylpentane remaining})}.$$

As used herein, the term "TEA" means tetraethylammonium cation.

As used herein, the term "MTEA" means methyltriethylammonium cation.

As used herein, the term "molecular sieve of the MCM-22 family" (or "material of the MCM-22 family" or "MCM-22 family material" or "MCM-22 family zeolite") includes one or more of:

(i) molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

(ii) molecular sieves made from a common second degree building block, being a 2-dimensional tiling of such MWW framework topology unit cells, forming a monolayer of one unit cell thickness, preferably one c-unit cell thickness;

(iii) molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks may be in a regular fashion, an irregular fashion, a random fashion, or any combination thereof; and (iv) molecular sieves made by any regular or random 2-dimensional or 3-dimensional combination of unit cells having the MWW framework topology.

The MCM-22 family includes those molecular sieves having an X-ray diffraction pattern including d-spacing maxima at 12.4±0.25, 6.9±0.15, 3.57±0.07 and 3.42±0.07 Angstrom. The X-ray diffraction data used to characterize the material are obtained by standard techniques using the K-alpha doublet of copper as incident radiation and a diffractometer equipped with a scintillation counter and associated computer as the collection system.

As used herein, the term "molecular sieve" is used synonymously with the term "zeolite".

The term "aspect ratio" when used in reference to the primary crystals is defined as the longest dimension of the crystallite divided by the width of the crystallite, where the width of the crystallite is defined as the dimension of the crystallite in the middle of that longest dimension in a direction orthogonal to that longest dimension, as measured by TEM.

As used herein, the term "primary crystal" denotes a single, indivisible crystal in contrast to an agglomerate. Primary crystals typically adhere together through weak physical interactions (rather than chemical bonds) to form agglomerates. The words "crystal" and "crystallite" are used herein interchangeably.

Catalyst Composition

The catalyst composition employed in the process of the invention comprises (i) a zeolite, (ii) 0.001 wt. % to 20.0 wt. % of at least one first metal, and (iii) 0.001 wt. % to 20.0 wt. % of at least one second metal, each wt. % based on the weight of the catalyst composition, wherein said catalyst composition is treated with a source of sulfur, preferably, in one or more steps at temperatures in the range 204° C. (400° F.) up to about 480° C. (900° F.) or treated with a source of steam, preferably, which comprises up to about 100% steam at temperatures in the range of about 260° C. (500° F.) to about 649° C. (1200° F.).

The zeolite of the catalyst composition has a constraint index of less than 12; or a constraint index of less than 10, or less than 8, or less than 6, or less than 4, or less than 2, or less than 1. The constraint index of the zeolite may be in the range of 3 to 12, or in the range of 5 to 9, or in the range of 0.6 to 3, or in the range of 0.3 to 0.6.

The zeolites which have a constraint index of less than 12 include and are selected from at least one of zeolite beta, ZSM-4, ZSM-5, ZSM-11, ZSM-12, ZSM-20, ZSM-22, ZSM-23, ZSM-35, ZSM-48, ZSM-50, ZSM-57, ZSM-58, MCM-68, a faujasite zeolite, a mordenite zeolite, the MCM-22 family materials, and mixtures thereof.

Zeolites which have a constraint index of 3 to 12 include and are selected from the group consisting of ZSM-5, ZSM-11, ZSM-22, ZSM-23, ZSM-35, ZSM-48, ZSM-57, ZSM-58, and mixtures thereof.

Zeolites which have a constraint index in the range of 5 to 9 include and are selected from the group consisting of ZSM-5, ZSM-11, ZSM-22, ZSM-23, and mixtures thereof.

Zeolites which have a constraint index in the range of 0.6 to 3 include and are selected from the group consisting of zeolite beta, ZSM-12, ZSM-50, a MCM-22 family material, and mixtures thereof.

Zeolites which have a constraint index of less than 3 include and are selected from the group consisting of zeolite beta, ZSM-4, ZSM-12, ZSM-20, ZSM-50, a MCM-22 family material, MCM-68, a mordenite zeolite including TEA-mordenite, meso-mordenite, a faujasite zeolite including REY, Deal Y. Mixtures of these zeolites which have a constraint index of less than 3 are contemplated.

Zeolites which have a constraint index in the range of 0.3 to 0.6 include ZSM-4, ZSM-20, a mordenite zeolite including TEA-mordenite, meso-mordenite, a faujasite zeolite including REY, Deal Y. Mixtures of these zeolites which have a constraint index in the range of 0.3 to 0.6 are contemplated.

ZSM-4 is described in U.S. Pat. No. 4,021,447. ZSM-5 is described in U.S. Pat. No. 3,702,886. ZSM-11 is described in U.S. Pat. No. 3,709,979. ZSM-12 is described in U.S. Pat. No. 3,832,449. ZSM-22 is described in U.S. Pat. No. 5,336,478. ZSM-23 is described in U.S. Pat. No. 4,076,842. ZSM-35 is described in U.S. Pat. No. 4,016,245. ZSM-48 is described in U.S. Pat. No. 4,375,573. ZSM-50 is described in U.S. Pat. No. 4,640,829, and ZSM-57 is described in U.S. Pat. No. 4,873,067. ZSM-58 is described in U.S. Pat. No. 4,698,217. MCM-68 is described in U.S. Pat. No. 6,049,018.

Constraint index and a method for its determination are described in U.S. Pat. No. 4,016,218, referenced above. The entire contents of each of the aforementioned patents are incorporated herein by reference.

The mordenite zeolite has a mesopore surface area of greater than 30 $m^2/g$ and comprising agglomerates composed of primary crystallites, wherein said primary crystallites have an average primary crystal size as measured by TEM of less than 80 nm and an aspect ratio of less than 2. This mordenite zeolite is referred to as "meso-mordenite" due to its high meso-porosity.

The MCM-22 family material includes and is selected from the group consisting of MCM-22, PSH-3, SSZ-25, MCM-36, MCM-49, MCM-56, ERB-1, EMM-10, EMM-10-P, EMM-12, EMM-13, UZM-8, UZM-8HS, ITQ-1, ITQ-2, ITQ-30 and mixtures of two or more thereof.

Materials of the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), ITQ-30 (described in International Patent Publication No. 2005/118476), MCM-36 (described in U.S. Pat. No. 5,250,277), MCM-49 (described in U.S. Pat. No. 5,236,575), MCM-56 (described in U.S. Pat. No. 5,362,697) and mixtures of two or more thereof.

Related zeolites to be included in the MCM-22 family are UZM-8 (described in U.S. Pat. No. 6,756,030) and UZM-8HS (described in U.S. Pat. No. 7,713,513), UZM-37 (described in U.S. Pat. No. 8,158,105), all of which are also suitable for use as the molecular sieve of the MCM-22 family. Typically, the molecular sieve of the MCM-22 family is in the hydrogen form and having hydrogen ions, for example, acidic. The entire contents of each of the aforementioned patents are incorporated herein by reference.

In one or more embodiments, the mordenite zeolite which has a very small crystal size and a high mesopore surface area is referred to as meso-mordenite, as defined herein. This meso-mordenite zeolite is synthesized from TEA or MTEA structure directing agents and has a mesopore surface area of greater than 30 $m^2/g$; and said mordenite zeolite comprising agglomerates composed of primary crystallites, wherein said primary crystallites have an average primary crystal size as measured by TEM of less than 80 nm and an aspect ratio of less than 2. The very small primary crystal size promotes access of reactant compounds to the active sites within the pores of the mordenite, thereby increasing catalytic efficiency.

The meso-mordenite zeolite comprises agglomerates, typically irregular agglomerates. The agglomerates are composed of primary crystallites which have an average primary crystal size as measured by TEM of less than 80 nm, preferably less than 70 nm and more preferably less than 60 nm, for example, less than 50 nm. The primary crystallites may have an average primary crystal size as measured by TEM of, for example, greater than 20 nm, optionally greater than 30 nm.

Optionally, the primary crystals of the meso-mordenite zeolite have an average primary crystal size of less than 80 nm, preferably less than 70 nm, and in some cases less than 60 nm, in each of the a, b and c crystal vectors as measured by X-ray diffraction. The primary crystallites may optionally have an average primary crystal size of greater than 20 nm, optionally greater than 30 nm, in each of the a, b and c crystal vectors, as measured by X-ray diffraction.

The meso-mordenite zeolite will generally comprise a mixture of agglomerates of the primary crystals together with some unagglomerated primary crystals. The majority of the meso-mordenite zeolite, for example, greater than 80 wt. % or greater than 90 wt. % will be present as agglomerates of primary crystals. The agglomerates are typically of irregular form. For more information on agglomerates please see Walter, D. (2013) Primary Particles—Agglomerates—Aggregates, in Nanomaterials (ed. Deutsche Forschungsgemeinschaft (DFG)), Wiley-VCH Verlag GmbH & Co. KGaA, Weinheim, Germany. doi: 10.1002/9783527673919, pages 1-24. Usefully, the meso-mordenite zeolite is not an aggregate.

Optionally, the meso-mordenite zeolite comprises at least 50 wt. %, preferably at least 70 wt. %, advantageously at least 80 wt. %, more preferably at least 90 wt. %, based on the weight of the catalyst composition, and optionally substantially consists of said irregular agglomerates composed of primary crystallites having a primary crystal size of less than 80 nm, preferably less than 70 nm, and more preferably less than 60 nm, for example, less than 50 nm. Preferably, the meso-mordenite zeolite of the invention comprises less than 10% by weight of primary crystallites having a size of more than 80 nm as assessed by TEM. Preferably, the meso-mordenite zeolite of the invention is composed of said irregular agglomerates composed of crystallites having a crystal size as measured by TEM of less than 80 nm. Preferably, the meso-mordenite zeolite of the invention is substantially free, for example, contains less than 10% by number as assessed by TEM, of needle or platelet crystals.

Preferably, said primary crystallites of the meso-mordenite zeolite of the invention have an aspect ratio of less than 3.0, more preferably less than 2.0, wherein the aspect ratio is defined as the longest dimension of the crystallite divided by the width of the crystallite, where the width of the crystallite is defined as the dimension of the crystallite in the middle of that longest dimension in a direction orthogonal to that longest dimension, as measured by TEM.

Said agglomerates of said primary crystallites are typically of irregular form and may be referred to as being "secondary" particles because they are formed of agglomerates of the crystallites, which are the "primary" particles.

The primary crystallites may have a narrow particle size distribution such that at least 90% of the primary crystallites by number have a primary crystal size in the range of from 20 to 80 nm, preferably in the range of from 20 to 60 nm, as measured by TEM.

The meso-mordenite zeolite has a mesopore surface area as measured by BET of greater than 30 m$^2$/g, preferably greater than 40 m$^2$/g, and in some cases greater than 45 m$^2$/g.

The meso-mordenite zeolite preferably has a total surface area of greater than 500 m$^2$/g, more preferably greater than 550 m$^2$/g, and in some cases greater than 600 m$^2$/g. The total surface area includes the surface area of the internal pores (zeolite surface area) and also the surface area on the outside of the crystals (the external surface area). The total surface area is measured by BET.

Preferably, the ratio of the meso-mesopore surface area to the total surface area for the meso-mordenite zeolite is greater than 0.05.

The meso-mordenite zeolite preferably has a mesopore volume of greater than 0.1 ml/g, more preferably greater than 0.12 ml/g, and in some cases greater than 0.15 ml/g.

The molar ratio Si:Al$_2$ of the meso-mordenite zeolite of the invention is preferably greater than 10 and may be in the range of, for example, from 10 to 60, preferably from 15 to 40. The molar ratio Si:Al$_2$ of the post-treated mordenite zeolite is preferably in the range of from 40 to 300, more preferably from 60 to 150.

The characterization of meso-mordenite and its method of making is further described in U.S. Publication No. 2016-0221832, the contents of which are incorporated by reference in its entirety.

In addition to the zeolite, the catalyst composition comprises at least one first metal, or compounds thereof, and a different at least one second metal, or compounds thereof. The first metal is in Group 6 of the Periodic Table. The second metal is in Group 9 or Group 10 of the Periodic Table. The first metal in Group 6 includes, but is not limited to, one or more of molybdenwn (Mo) or tungsten (W), and compounds containing neutral metals or ions thereof. The second metal in Group 9 includes, but is not limited to, one or more of cobalt (Co), rhodium (Rh) and iridium (Ir), and compounds containing neutral metals or ions thereof, preferably cobalt. The second metal in Group 10 includes, but is not limited to, one or more of nickel (Ni), palladium (Pd), platinum (Pt), preferably nickel.

In one or more embodiments of the invention, the first metal in Group 6 of the catalyst composition may be in the range from about 0.001 wt. % to 20 wt. %, or from greater than or equal to 0.005 wt. % up to at least 15.0 wt. %, or from about 0.10 wt. % up to at least 10.0 wt. %, based on the weight of the catalyst composition. Alternatively, the first metal in Group 6 of the catalyst composition comprises from at least about 0.001 wt. %, or 0.005 wt. %, or 0.01 wt. %, or 0.05 wt. %, or 0.10 wt. % up to about 1.0 wt. %, 2.5 wt. %, 5.0 wt. %, or 7.5 wt. %, or 10.0 wt. %, or 15.0 wt. %, or 20.0 wt. %, based on the weight of the catalyst composition.

In one or more embodiments of the invention, the second metal in Group 9 or Group 10 of the catalyst composition may be in the range from about 0.001 wt. % to 20 wt/%, or from greater than or equal to 0.001 wt. % up to at least 15.0 wt. %, or from about 0.005 wt. % up to at least 10.0 wt. %, based on the weight of the catalyst composition. Alternatively, the second metal in Group 9 or Group 10 of the catalyst composition comprises from at least about 0.001 wt. %, or 0.005 wt. %, or 0.01 wt. %, or 0.05 wt. %, or 0.10 wt. % up to about 1.0 wt. %, 2.5 wt. %, 5.0 wt. %, or 7.5 wt. %, or 10.0 wt. %, or 15.0 wt. %, or 20.0 wt. %, based on the weight of the catalyst composition. The percentages above in this paragraph are for the Group 9 metal alone or the Group 10 metal alone, or a combination thereof.

The first metal and/or the second metal, may be provided on the catalyst composition in any manner, for example, by conventional methods such as impregnation or ion exchange of the zeolite and/or the second zeolite with a solution of a compound of the relevant metal before or after forming the catalyst particle.

In a preferred embodiment, the catalyst composition of this invention comprises (i) a zeolite which comprises zeolite beta, ZSM-5, ZSM-12 or a mordenite zeolite which is synthesized from TEA or MTEA, (ii) 0.001 wt. % to 20.0 wt. % of at least one first metal comprising molybdenum or tungsten, based on the weight of the catalyst composition, and (iii) 0.001 wt. % to 20.0 wt. % of at least one second metal comprising cobalt or nickel, based on the weight of the catalyst composition, said mordenite zeolite having a mesopore surface area of greater than 30 m²/g and said mordenite comprises agglomerates composed of primary crystallites, wherein said primary crystallites have an average primary crystal size as measured by TEM of less than 80 nm and an aspect ratio of less than 2, wherein said catalyst composition is treated with a source of sulfur in one or more steps at temperatures in the range 204° C. (400° F.) up to about 480° C. (900° F.) or treated with a source of steam which comprises up to about 100% steam at temperatures in the range of about 260° C. (500° F.) to about 649° C. (1200° F.).

Catalyst Binders

It may be desirable to incorporate another material into the zeolite in the catalyst composition that is resistant to the temperatures and other conditions employed in the transalkylation process of the invention. Such materials include active and inactive materials and synthetic or naturally occurring zeolites, as well as inorganic materials such as clays, silica and/or metal oxides such as alumina. The inorganic material may be either naturally occurring, or in the form of gelatinous precipitates or gels including mixtures of silica and metal oxides.

The catalyst composition of this invention further comprises at least one binder selected from the group consisting of alumina, silica, clay, titania, zirconia and a mixture of two or more thereof. Use of a material in conjunction with the zeolite, i.e., combined therewith or present during its synthesis, which itself is catalytically active, may change the conversion and/or selectivity of the catalyst composition. Inactive materials suitably serve as diluents to control the amount of conversion so that transalkylated products can be obtained in an economical and orderly manner without employing other means for controlling the rate of reaction. These catalytically active or inactive materials may be incorporated into, for example, naturally occurring clays, for example bentonite and kaolin, to improve the crush strength of the catalyst composition under commercial operating conditions. It is desirable to provide a catalyst composition having good crush strength because in commercial use, it is desirable to prevent the catalyst composition from breaking down into powder-like materials.

Naturally occurring clays that can be composited with the zeolite as a binder for the catalyst composition include the montmorillonite and kaolin family, which families include the subbentonites, and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolite may be composited with a porous matrix binder material, such as an inorganic oxide selected from the group consisting of silica, alumina, zirconia, titania, thoria, beryllia, magnesia, and combinations thereof, such as silica-alumina, silica-magnesia, silica-zirconia, silica-thoria, silica beryllia silica-titanic, as well as ternary compositions such as silica-alumina-thoria, silica-alumina-zirconia, silica-alumina-magnesia and silica-magnesia-zirconia. It may also be advantageous to provide at least a part of the foregoing porous matrix binder material in colloidal form to facilitate extrusion of the catalyst composition.

Each zeolite is usually admixed with the binder or matrix material so that the final catalyst composition contains the binder or matrix material in an amount ranging from 0 to 100 wt. %, such as for example from 5 wt. % to 90 wt. %, and typically from 10 wt. % to 60 wt. %, based on the weight of the catalyst composition.

Treatment of the Catalyst Composition by Sulfiding and/or Steaming

The catalyst composition is treated to minimize the saturation of the desirable light aromatic products, without substantially inhibiting olefin saturation.

One method to minimize the saturation of the desirable light aromatic product is by sulfiding in which the catalyst composition is treated with a source of sulfur, such as, for example, hydrogen sulfide, $H_2S$. Effective treatment is accomplished by contacting the catalyst composition with a source of sulfur in one or more steps (stagewise) at a temperature ranging from about 204° C. up to about 480° C. (from about 400° F. up to about 900° F.).

In one embodiment, the source of sulfur is contacted with the catalyst composition by adding it to the hydrocarbon feedstock in a concentration ranging from about 50 ppmw sulfur to about 10,000 ppmw sulfur.

Any sulfur compound that will decompose to form $H_2S$ and a light hydrocarbon at about 480° C. (900° F.) or less will be a suitable source of sulfur. Examples of appropriate sources of sulfur include carbon disulfide and alkylsulfides, such as methylsulfide, dimethylsulfide, dimethyldisulfide, diethylsulfide and dibutyl sulfide. Sulfur treatment can be considered sufficient when sulfur breakthrough occurs; that is, when sulfur appears in the liquid effluent.

In another embodiment, the source of sulfur can be contacted with the catalyst composition via a carrier gas, typically, an inert gas such as hydrogen or nitrogen.

In still another embodiment, the sulfur treatment may be initiated by incorporating a source of sulfur into the feed and continuing sulfur treatment for a few days, typically, up to 10 days, more specifically, from one to five days. The progress of the sulfur treatment can be monitored by measuring the concentration of sulfur in the product off gas. During this treatment, the sulfur concentration in the off gas should range from about 20 ppmw to about 500 ppmw sulfur, preferably about 30 ppmw to 250 ppmw.

Continuously co-feeding a source of sulfur has been found to maintain a sufficiently minimal aromatics hydrogenation activity. The catalyst composition can be contacted with sulfur during service by co-feeding sulfur to the reactor in varied amounts via the hydrogen stream entering the reactor or the hydrocarbon feedstock. The sulfur can be continuously added to the feedstock throughout the process cycle or the sulfur can be intermittently continuously added in which this sulfur is co-fed continuously for a period of time, discontinued, then cofed again.

Another method to minimize the saturation of the desirable light aromatic product is by steaming in which the catalyst composition is treated with a source of steam. The steam treatment is effectuated by contacting catalyst composition with up to about 100% steam, or from about 5 up to 100% steam, at a temperature in a range from at least about 260° C. (500° F.) up to about 649° C. (1200° F.) in one or more temperature steps, for at least about one hour, specifically about 1 to about 20 hours at a pressure of 100 kPa to 2500 kPa.

Any one or a combination of these methods may be practiced in-situ and/or ex-situ.

Regeneration of Catalyst Composition

After contacting the catalyst composition with the hydrocarbon feed, the catalyst composition may be deactivated due to coking or metal agglomeration. The deactivated catalyst composition can be regenerated conveniently by coke burning with a stream comprising oxygen or oxygen containing compounds, such as, ozone, oxochlorine, carbon dioxide or the like, metal re-dispersing using oxdization-reduction cycle, oxochloride treatment or the like, washing with liquid hydrocarbons or aqueous solution of inorganic and/or organic chemical compounds, such as, water, ethanol, acetone, or the like, or rejuvenation with a stream comprising hydrogen. Regeneration or rejuvenation can be performed at a temperature range from ambience to about 600° C., a pressure range of about 100 kPa-a to about 5000 kPa-a, and WHSV of about 0.2 $hr^{-1}$ to about 100 $hr^{-1}$.

Feedstock

The feedstock used in the process of the invention comprises one or more aromatic compounds containing at least 8 carbon atoms, for example, $C_{8+}$ aromatic hydrocarbons. Specific comprising $C_{8+}$ aromatic hydrocarbons include ethylbenzene and dimethylbenzene isomers. Typically, such $C_{8+}$ aromatic hydrocarbons comprise aromatic compounds having a boiling point in the range of about 135° C. to about 230° C. at atmospheric pressure.

In one or more embodiments, such feedstock comprises aromatic compounds having 9 or more carbon atoms, for example, $C_{9+}$ aromatic hydrocarbons. Specific $C_{9+}$ aromatic compounds found in a typical feed include mesitylene (1,3,5-trimethylbenzene), durene (1,2,4,5-tetramethylbenzene), hemimellitene (1,2,4-trimethylbenzene), pseudocumene (1,2,4-trimethylbenzene), ethyltoluene, ethylxylene, 1,2-methylethylbenzene, 1,3-methylethylbenzene, 1,4-methylethylbenzene, propyl-substituted benzenes, butyl-substituted benzenes, dimethylethylbenzenes, methylpropylbenzene, methylbutylbenzene, and a mixture of two or more thereof).

Suitable sources of the $C_{9+}$ aromatics are any $C_{9+}$ fractions from any refinery process that is rich in aromatics. This aromatics fraction contains a substantial proportion of $C_{9+}$ aromatics, for example, at least 80 wt. % $C_{9+}$ aromatics, wherein preferably at least 80 wt. %, and more preferably more than 90 wt. %, of the hydrocarbons will range from $C_9$ to $C_{12}$. Typical refinery fractions which may be useful include catalytic reformate, fluidized catalytic cracking (FCC) naphtha or thermoform catalytic cracking (TCC) naphtha.

The feedstock may also further comprise benzene or toluene or a mixture of benzene and toluene. Thus, in one practical embodiment, the feed to the transalkylation reactor comprises ethylbenzene, $C_{9+}$ aromatics hydrocarbons and toluene. The feedstock may also include recycled/unreacted/produced benzene, toluene, ethylbenzene, and $C_{9+}$ aromatics that is obtained by distillation of the effluent product of the process which comprises said lighter aromatic products. Typically, toluene constitutes from about 5 wt. % to about 90 wt. % and $C_{9+}$ constitutes from about 10 wt. % to about 95 wt. % of the feedstock. In a typical light feedstock, toluene constitutes from about 40 wt. % to about 90 wt. %, such as from 50 wt. % to 70 wt. % of the entire feed, whereas the $C_{9+}$ aromatics component constitutes from 10 wt. % to 60 wt. %, such as from 30 wt. % to 50 wt. %, of the entire feedstock to the transalkylation reaction zone. In a typical heavy feed, toluene constitutes from about 15 wt. % to about 50 wt. %, such as from 25 wt. % to 40 wt. % of the entire feed, whereas the $C_{9+}$ aromatics component constitutes from 50 wt. % to 85 wt. %, such as from 60 wt. % to 75 wt. %, of the entire feed to the transalkylation reaction zone.

Hydrocarbon Conversion Process

The process for the conversion of a feedstock comprising $C_{8+}$ aromatic hydrocarbons to lighter aromatic products comprises the steps of contacting said feedstock and optionally hydrogen in the presence of any one of the catalyst compositions of this invention under suitable conversion conditions to produce said lighter aromatic products comprising benzene, toluene and xylene. The suitable conversion conditions are effective to dealkylate and transalkylate said $C_{8+}$ aromatic hydrocarbons. Preferably, the hydrocarbon conversion takes place in the presence of hydrogen, more preferably at a molar ratio of hydrogen to hydrocarbon ($H_2$/HC) of from 0.1 to 10, even more preferably of from 0.5 to 5, such as 0.6 to 4.

In a preferred embodiment, the catalyst composition is treated with a source of sulfur and/or a source of steam, and comprises: (i) at least one zeolite selected from the group consisting of zeolite beta, ZSM-4, ZSM-5, ZSM-11, ZSM-12, ZSM-20, ZSM-22, ZSM-23, ZSM-35, ZSM-48, ZSM-50, ZSM-57, ZSM-58, MCM-68, a faujasite zeolite, a mordenite zeolite, a MCM-22 family material, or a mixture thereof, (ii) 0.001 wt. % to 20.0 wt. % of at least one first metal, said first metal being in Group 6 of the Periodic Table, based on the weight of said catalyst composition, and (iii) 0.001 wt. % to 20.0 wt. % of at least one second metal, said second metal being in Group 9 or Group 10 of the Periodic Table, based on the weight of said catalyst composition.

In another preferred embodiment, the catalyst composition is a treated catalyst composition which is made by the method comprising the steps of: (a) providing a catalyst composition comprising at least one zeolite selected from the group consisting of zeolite beta, ZSM-4, ZSM-5, ZSM-11, ZSM-12, ZSM-20, ZSM-22, ZSM-23, ZSM-35, ZSM-48, ZSM-50, ZSM-57, ZSM-58, MCM-68, a faujasite zeolite, a mordenite zeolite, a MCM-22 family material, or a mixture thereof; (b) contacting said catalyst composition with a source of a first metal or compounds thereof and a source of a second metal or compounds thereof to form a metal-containing catalyst composition, wherein said first metal is in Group 6 of the Periodic Table, wherein said second metal is in Group 9 or Group 10 of the Periodic Table, wherein said metal-containing catalyst composition comprises 0.001 wt. % to 20.0 wt. % of said first metal, and 0.001 wt. % to 20.0 wt. % of said second metal, each weight % based on the weight of the catalyst composition; and (c) treating said metal-containing catalyst composition with a source of sulfur and/or a source of steam to form said treated catalyst composition.

The lighter aromatic products made by the process comprises at least benzene, toluene and xylene.

The conversion conditions typically include a temperature ranging from about 340° C. to about 515° C., such as from about 400° C. to about 454° C.; a pressure from about 380 to kPa-a about 4240 kPa-a, such as from about 1480 kPa-a to about 3550 kPa-a; a hydrogen to hydrocarbon molar ratio from about 1 to about 5, such as from about 1 to about 3 and a WHSV of about 0.2 $hr^{-1}$ to about 100 $hr^{-1}$, such as from 1 $hr^{-1}$ to about 100 $hr^{-1}$. The transalkylation reaction conditions are sufficient to convert the heavy aromatic feed to a product containing substantial quantities of $C_6$-$C_8$ aromatic compounds, such as benzene, toluene and xylenes, especially benzene and xylene. The transalkylation reaction conditions also are sufficient to convert the ethylbenzene in the feed to benzene and ethane.

The process can be conducted in any appropriate reactor including a radial flow, fixed bed, continuous flow or fluid bed reactor. In one alternative, the reactor for contacting said feedstock under said suitable conversion conditions comprises at least one single fixed catalyst bed of said catalyst composition. In another alternative, the reactor for contacting said feedstock under said suitable conversion comprises at least one moving catalyst bed of said catalyst composition.

EXAMPLES

The following examples illustrate the present invention. Numerous modifications and variations are possible and it is to be understood that within the scope of the appended claims, the invention may be practiced otherwise than as specifically described herein.

EXPERIMENTAL

Measurement of Average Primary Particle Size and Primary Particle Size Distribution The measurement of average primary particle size and primary particle size distribution was carried out as follows. Several TEM photographs of the zeolite sample were taken; primary particles were identified and measured. For each primary particle having an aspect ratio greater than 1, the longest dimension was identified by drawing a line between the two points at the edge of the particle which were the furthest apart. Then the length of the primary particle along a 45° diagonal to that longest dimension and passing through the mid-point of that longest dimension was measured as the particle size. Each measurement was grouped by being assigned to one of about 10 particle size ranges covering the range of sizes found in the sample. More than 300 primary particles were measured and then the numbers in each particle size range were plotted to show the particle size distribution. The percent (%) crystals value on the y-axis was calculated from: Number of particles in each group/total number of particles measured multiplied by 100. The average particle size was calculated as the arithmetical mean based on the grouped results.

Measurement of Total Surface Area and Mesopore Surface Area by BET

The total BET and the t-Plot micropore surface area were measured by nitrogen adsorption/desorption with a Micromeritics Tristar II 3020 instrument after degassing of the calcined zeolite powders for 4 hrs at 350° C. The mesopore surface area was obtained by the subtraction of the t-plot micropore from the total BET surface area. The mesopore volume was derived from the same data set. More information regarding the method can be found, for example, in "Characterization of Porous Solids and Powders: Surface Area, Pore Size and Density", S. Lowell et al., Springer, 2004.

X-Ray Diffraction Patterns

The X-ray diffraction data (powder XRD or XRD) were collected with a Bruker D4 Endeavor diffraction system with a VANTEC multichannel detector using copper K-alpha radiation. The diffraction data were recorded by scanning mode with 0.018 degrees two-theta, where theta is the Bragg angle, and using an effective counting time of about 30 seconds for each step.

Measurement of the Crystal Sizes in the a, b and c Vectors

The crystal sizes in the a, b and c crystal vectors were calculated based on the three (200), (020) and (002) peaks in the X-ray diffraction patterns using the Scherrer equation (P. Scherrer, N. G. W. Gottingen, Math-Pys., 2, p. 96-100 (1918)). The method and its application to zeolites are also described in A. W. Burton, K. Ong. T. Rea, I. Y. Chan, Microporous and Mesoporous Materials, 117, p. 75-90 (2009). For the measurements described herein the Jade version 9.5.1 X-ray diffraction analysis software by Materials Data, Inc., was used to perform the calculation.

Alpha Value

The alpha value is a measure of the cracking activity of a catalyst composition and is described in U.S. Pat. No. 3,354,078 and in the Journal of Catalysis, Vol. 4, p. 527 (1965); Vol. 6, p. 278 (1966) and Vol. 61, p. 395 (1980), each incorporated herein by reference. The experimental conditions of the test used herein included a constant temperature of 538° C. and a variable flow rate as described in detail in the Journal of Catalysis, Vol. 61, p. 395 (1980).

Sulfiding Conditions

The catalyst was treated with 2% $H_2S$ at a flow rate of 15 sccm. The temperature was increased in two steps. The temperature was increased to 232° C. (450° F.) at 1° C./min (60° C./h) increments, and held there for 16 hours. Then, the temperature was increased to 343° C. (650° F.) at 1° C./min (60° C./h) increments, and held there for 6 hours.

Example 1

Meso-Mordenite Crystals

Meso-mordenite crystals were synthesized from a mixture prepared from 9,300 g of water, 804 g of tetraethylammonium bromide (TEABr) (50% solution), 2,544 g of Ultrasil PM Modified silica, 584 g of sodium aluminate solution (45%), and 612 g of 50% sodium hydroxide solution. Then, 30 g of mordenite seeds was added to the mixture. The mixture had the following molar composition:

$SiO_2/Al_2O_3$—26.1
$H_2O/SiO_2$—15.11
$OH^-/SiO_2$—0.29
$Na^+/SiO_2$—0.29
$TEA/SiO_2$—0.05

The mixture was reacted at 143.3° C. (290° F.) in a 20 liter (5-gal) autoclave with stirring at 250 RPM for 72 hours. The product was filtered, washed with deionized (DI) water and dried at 121° C. (250° F.). The XRD pattern of the as-synthesized material showed the typical pure phase of mordenite topology. The SEM of the as-synthesized material showed morphology of irregularly-shaped agglomerates composed of small crystallites of ≤0.05 μm. Smaller and more uniform crystals were produced from this improved synthesis as compared to prior art lower porosity mordenite crystals. The resulting as-synthesized meso-mordenite crystals showed a $SiO_2/Al_2O_3$ molar ratio of about 20.7.

The as-synthesized crystals meso-mordenite were converted into the hydrogen form by three ion exchanges with ammonium nitrate solution at room temperature, followed by drying at 121° C. (250° F.) and calcination at 538° C. (1000° F.) for 6 hours. The resulting H-formed meso-mordenite crystals had a total/(micro+meso) surface area of 637/(580+56) m²/g and meso-pore volume of 0.43 cc/g. The hexane sorption was 53.3 mg/g and the Alpha value was 1,200. Based on the outcome of this example, it was concluded that small and uniform mordenite crystals with higher mesopore volume and surface area could be synthesized from reaction mixtures with higher solids and lower reaction temperature.

Example 2

Meso-Mordenite/ZSM-5/Alumina Catalyst (65/15/20 by wt.)

A catalyst was made from a mixture of 65 parts (basis: calcined 538° C.) of the meso-mordenite crystal from Example 1 and 15 parts ZSM-5 (made according to U.S. Pat. No. 3,702,886, basis: calcined 538° C., $Si/Al_2$ approx. 60/1 molar) and 20 parts alumina (basis: calcined 538° C.) in a muller. Sufficient water was added to produce an extrudable paste on an extruder. The mixture of meso-mordenite, ZSM-5, alumina, and water was extruded into an extrudate, and then dried at 121° C. The dried extrudate was calcined in nitrogen ($N_2$) at 538° C. to decompose and remove the organic template. The $N_2$-calcined extrudate was humidified with air saturated with water and exchanged with 1 N ammonium nitrate to remove sodium. After ammonium nitrate exchange, the extrudate was washed with deionized water to remove residual nitrate ions prior to drying. The ammonium-exchanged extrudate was dried at 121° C. and calcined in air at 538° C. After air calcination, properties of the resulting catalyst were: Alpha Value=570; and hexane sorption 53.5 mg/g.

Example 3

Un-Sulfided Co/Mo on Meso-Mordenite/ZSM-5/Alumina Catalyst

The extrudate from Example 2 (65/15/20 by wt.) was impregnated with 1.8 wt. % Co as cobalt (II) acetate and 5 wt. % molybdenwn as ammonium molybdate tetrahydrate via incipient wetness. The catalyst was calcined in air at 538° C. for 3 hours.

Example 4

Sulfided Co/Mo on Meso-Mordenite/ZSM-5/Alumina Catalyst

A portion of the catalyst of Example 3 was sulfided with $H_2S$ as Example 4, prior to performance testing. The remaining portion of the catalyst of Example 3 remained unsulfided.

Example 5

Sulfided Mo on Meso-Mordenite/ZSM-5/Alumina Catalyst

The extrudate from Example 2 (65/15/20 by wt.) was impregnated with 5 wt. % molybdenum as ammonium molybdate tetrahydrate via incipient wetness. The catalyst was calcined in air at 538° C. for 3 hours. The catalyst of this Example 5 was sulfided with $H_2S$ prior to performance testing.

Example 6

Performance Evaluation of Examples 3 to 5

Sulfided metal function was evaluated in a hydrocarbon conversion reaction of $C_{8+}$ aromatics, toluene and benzene. An unsulfided cobalt-molybdenum (Co/Mo) system, Example 3, was compared to a sulfided Co/Mo system, Example 4, and a sulfided Mo metallic system, Example 5. The evaluation was performed in a reactor using the feed blends identified in Table 1 below.

TABLE 1

| Feed Blends | | |
|---|---|---|
| Component | Example 3 Weight % | Example 4 and 5 Weight % |
| Benzene | 0.3 | 0.00 |
| Toluene | 39.7 | 39.00 |
| Ethylbenzene | 0.03 | 0.02 |
| O-Xylene | 0.91 | 0.92 |
| M-Xylene | 0.17 | 0.17 |
| Other $C_9$ Paraffins | 0.07 | 0.63 |
| P-Xylene | 0.07 | 0 |
| N-Propylbenzene | 0.18 | 3.59 |
| Isopropylbenzene | 3.54 | 0.60 |
| 1-Methyl-2-Ethylbenzene | 0.11 | 4.87 |
| 1-Methyl-3-Ethylbenzene | 11.81 | 12.29 |
| 1-Methyl-4-Ethylbenzene | 5.17 | 4.99 |
| 1,2,3-Trimethylbenzene | 2.54 | 3.21 |
| 1,2,4-Trimethylbenzene | 18.12 | 18.73 |
| 1,3,5-Trimethylbenzene | 5.40 | 5.60 |
| Indane | 0.79 | 0.80 |
| Other $C_{10}$ Paraffins | 0.11 | 0.00 |
| 1-Methyl-3-N-Propylbenzene | 0.11 | 0.83 |
| 1-Methyl-4-N-Propylbenzene | 0.21 | 0.39 |
| 1-Methyl-3-Isopropylbenzene | 0.78 | 0.08 |
| 1-Methyl-4-Isopropylbenzene | 0 | 0.04 |
| 1,2-Diethylbenzene | 0.13 | 0.04 |
| 1,3-Diethylbenzene | 0.36 | 0.38 |
| 1,4-Diethylbenzene | 0.35 | 0.38 |
| 1,2-Dimethyl-3-Ethylbenzene | 0.05 | 0.05 |
| 1,2-Dimethyl-4-Ethylbenzene | 0.34 | 0.34 |
| 1,3-Dimethyl-2-Ethylbenzene | 0 | 0.04 |
| 1,3-Dimethyl-4-Ethylbenzene | 0.24 | 0.21 |
| 1,3-Dimethyl-5-Ethylbenzene | 0 | 0.00 |
| 1,4-Dimethyl-2-Ethylbenzene | 0.22 | 0.27 |
| 1,2,3,4-Tetramethylbenzene | 0.02 | 0.00 |
| 1,2,3,5-Tetramethylbenzene | 0.10 | 0.10 |
| 1,2,4,5-Tetramethylbenzene | 0.07 | 0.08 |
| Naphthalene | 0.02 | 0.02 |
| M-Indanes | 0 | 0.00 |
| Other $C_{10}$ Aromatics | 7.46 | 1.29 |
| 1-Methyl-Naphthalene | 0.00 | 0.00 |
| 2-Methyl-Naphthalene | 0.00 | 0.01 |
| Other $C_{11}$ Aromatics | 0.01 | 0.02 |
| Total | 100.0 | 100.0 |

Three to four grams of each catalyst was loaded into the reactor. The catalysts from Examples 4 and 5 were sulfided with 2% $H_2S$ as described above. Thereafter, 100% hydrogen replaced the 2% $H_2S$, and the temperature was then increased to 430° C. (806° F.). Liquid feed was introduced for a 12 hour de-edging period. Conditions of the de-edging and temperature scans are provided below. Following the de-edging period, conditions were modified and a temperature scans were performed on the Feed Blends. Example 3 was also evaluated without the sulfiding step, instead with a reduction step by heating in the presence of hydrogen and activated at 410° C. (770° F.).

Conditions of the de-edging and subsequent reaction conditions were: De-edging Conditions: WHSV=3 $hr^{-1}$, $H_2$/HC=1, temperature=430° C. (806° F.) for 12 hours, and pressure=2696 kPa (391 psig). Temperature Scan Conditions: WHSV=3 $hr^{-1}$, $H_2$/HC=3, temperature=12 hours at 355° C. (671° F.), then 12 hours at 380° C. (716° F.), then 12 hours at 405° C. (761° F.), and then 12 hours at 430° C. (806° F.), and pressure=2696 kPa (391 psig). The product was analyzed by on-line gas chromatography (GC). Performance comparisons for Examples 3 to 5 are set forth in Table 2, below.

TABLE 2

Performance of Sulfided Base Metal Function

| Example Numbers | Catalyst Descriptions | Ethyl-Aromatic Conversion at 380° C. (716° F.) % | Tol/C$_9$/C$_{10}$ Conversion at 380° C. (716° F.) % | Xylenes at 380° C. 716° F.) % | Ring Loss at 380° C. (716° F.) % | Methane at 380° C. (716° F.) % | Ethane/Ethylene at 380° C. (716° F.) Molar ratio |
|---|---|---|---|---|---|---|---|
| 3 | Co/Mo (unsulfided) | 85 | 50 | 29.0 | 3.2 | 1.3 | N/A* |
| 4 | Co/Mo (sulfided) | 84 | 79 | 31.9 | 1.1 | 0.1 | 5000 |
| 5 | Mo (sulfided) | 91 | 76 | 31.9 | 2.6 | 0.1 | 4500 |

*N/A = Not analyzed.

As shown in Table 2, molybdenum and a combination of cobalt/molybdenum added via incipient wetness to a co-extrudate of meso-mordenite and ZSM-5 resulted in very good performance when sulfided. Without sulfiding, these types of metals perform significant hydrogenolysis (metal cleavage of carbon-carbon bonds from an aromatic ring), resulting in high methane formation. Xylene yields were high and ring loss was low. The low ring loss indicates that the metal function is not too active to avoid saturating a number of aromatic rings. The ethane/ethylene ratios are very high. Ethane/ethylene molar ratio is an indication of the effectiveness of the metal function in saturating olefins. As can be seen, the unsulfided Co/Mo catalyst shows significant hydrogenolysis activity (high methane yield) as well as lower transalkylation activity and xylenes yield as compared to the sulfided Co/Mo catalyst.

Example 7

Ni/W on Steamed 65/35 wt./wt. ZSM-12/Alumina Catalyst

A catalyst was made by mixing 65 parts (basis: calcined 538° C.) of ZSM-12 (basis: calcined 538° C. Si/Al$_2$ approx. 180/1 molar) and 35 parts alumina (basis: calcined 538° C.) in a muller. Sufficient water was added to produce an extrudable paste on an extruder. The mixture of ZSM-12, alumina, and water was extruded into an extrudate and then dried at 121° C. The dried extrudate was calcined in nitrogen (N$_2$) at 538° C. to decompose and remove the organic template. The N$_2$-calcined extrudate was humidified with air saturated with steam and exchanged with 1 N ammonium nitrate to remove sodium. After ammonium nitrate exchange, the extrudate was washed with deionized water to remove residual nitrate ions prior to drying. The ammonium-exchanged extrudate was dried at 121° C. and calcined in air at 538° C. The extrudate was then steamed for 5.25 hours at 482° C. in full steam. This steamed extrudate was then impregnated via incipient wetness with a bimetallic solution of nickel nitrate hexahydrate and ammonium metatungstate hydrate to a target of 3 wt. % Ni and 15 wt. % W. The catalyst was then calcined in air at 482° C.

Example 8

Fe on Steamed 65/35 wt./wt. ZSM-12/Alumina Catalyst

A catalyst was made by mixing 65 parts (basis: calcined 538° C.) of ZSM-12 (basis: calcined 538° C., Si/Al$_2$ approx. 180/1 molar) and 35 parts alumina (basis: calcined 538° C.) in a muller. Sufficient water was added to produce an extrudable paste on an extruder. The mixture of ZSM-12, alumina, and water was extruded into an extrudate and then dried at 121° C. The dried extrudate was calcined in nitrogen (N$_2$) at 538° C. to decompose and remove the organic template. The N$_2$-calcined extrudate was humidified with saturated air and exchanged with 1 N ammonium nitrate to remove sodium. After ammonium nitrate exchange, the extrudate was washed with deionized water to remove residual nitrate ions prior to drying. The ammonium-exchanged extrudate was dried at 121° C. and calcined in air at 538° C. The extrudate was then steamed for 5 hours at 482° C. in full steam. This steamed extrudate was then impregnated via incipient wetness with a solution of iron nitrate nonahydrate to a target of 3 wt. % Fe.

Example 9

Co/Mo on Steamed 65/35 wt./wt. on Meso-Mordenite/Alumina Catalyst

A catalyst was made by mixing 65 parts (basis: calcined 538° C.) of meso-mordenite crystal from Example 1, 35 parts of Versal 300 pseudoboehmite alumina (basis: calcined 538° C.), and bimetallic metal precursor solutions of cobalt (II) acetate tetrahydrate and ammonium heptamolybdate in a muller. Sufficient water was added to produce an extrudable paste on an extruder. The metal precursor solutions were added to meso-mordenite crystals (crush strength of 22.14 kg/cm; 124 lbs/in) or a mixture of meso-mordenite crystals and an alumina binder (crush strength of 26.43 kg/cm; 148 lbs/in). The mixture was extruded and dried at 121° C. overnight. The dried extrudate was calcined in nitrogen (N$_2$) at 538° C. to decompose and remove the organic template. The N$_2$-calcined extrudate was humidified with saturated air and exchanged with 1 N ammonium nitrate, or ammonium acetate, or ammonium chloride, or ammonium carbonate solutions to remove sodium. After ammonium nitrate exchange, the extrudate was washed with deionized water to remove residual nitrate ions prior to drying. The ammonium-exchanged extrudate was dried at 121° C. and calcined in air at 538° C. After air calcination, the extrudate was steamed for 2 hrs at 399° C. (750° F.). In H-form, the catalyst had an Alpha Value of 4.2, hexane cracking value of 2.4, a surface area of 358 (201+157) m$^2$/g, and Co/Mo wt./wt. of 2.08/12.7.

Example 10

Performance Evaluation of Examples 7 to 9

The catalysts of Examples 7 to 9 were evaluated in a hydrocarbon conversion reaction of $C_{8+}$ aromatics and toluene. These catalysts were evaluated in a reactor using a feed blend comprised of 60 wt. % of heavy aromatics (HAR), identified in Table 3 below, and 40 wt. % toluene.

TABLE 3

Heavy Aromatics (HAR) Composition
Heavy Aromatics (HAR)

| Component | wt. % |
|---|---|
| $C_8$ Aromatics | 0.2 |
| $C_9$ Aromatics | 73.7 |
| $C_{10}$ Aromatics | 23.7 |
| $C_{11+}$ Aromatics | 0.5 |
| Non-Aromatics | 0.6 |
| Online GC Heavies (>218° C.) | 1.2 |

The feed was passed over 2-5 g of catalyst loaded into reactor. The feed and hydrogen are premixed and vaporized before contacting the catalyst. Temperature is measured using a thermocouple situated in the reactor. The reactor is operated isothermally. The product mixtures obtained were analyzed using G.C. Concentrations of the various components in the product mixture in weight percentages based on the total weight of the product mixture were calculated based on the gas chromatography analysis data. Sulfiding of the catalysts was by continuous co-feed and accomplished using a 400 ppmv (volume) $H_2S$ in $H_2$ by adjusting the flow rate and the time of sulfiding until 3-4 times of the amount (by mole) of Ni, Fe and Mo, respectively, was deposited on the catalyst.

The reaction conditions for Examples 7 to 10 are shown in Table 4, below.

Performance results are shown in Tables 5A, 5B and 5C, below. As can be seen, the key findings are that the sulfided iron is less effective than other base metal combinations as evidenced by the higher inlet temperature to achieve conversion and the very low ethane/ethylene ratio, indicating that there is not quite enough metal activity. The sulfided Ni/W appears to have good metal function for heavy aromatics transalkylation. When tested in a single bed configuration, Ni/W over ZSM-12/alumina and Co/Mo over meso-mordenite/alumina have similar activity, while Fe over ZSM-12 has much lower activity with the same feed blend. However, Ni/W over ZSM-12/alumina and Fe over ZSM-12 have lower ethane/ethylene ratio as compared to Co/Mo over meso-mordenite/alumina.

TABLE 4

Reaction Conditions

| Example Number | Catalyst Descriptions | Pressure kPa (psig) | Weight Hourly Space Velocity (WHSV) $hr^{-1}$ | Reactor Inlet Temperature ° C. (° F.) | Reactor Temperature ° C. | $H_2$/Hydrocarbon (HC) Molar Ratio |
|---|---|---|---|---|---|---|
| 7 | Ni/W on ZSM-12/ Alumina | 2613 (379) | 3.0 | 415 (779) | 415 | 2.0 |
| 8 | Fe on ZSM-12/Alumina | 2606 (378) | 3.0 | 426 (799) | 426 | 2.0 |
| 9 | Co/Mo on Meso-Mordenite/ Alumina | 2606 (378) | 3.1 | 361 (681) | 360 | 2.0 |

TABLE 5A

Performance Results - Catalyst

| Example Number | Catalyst Descriptions | De-ethylation % | De-propylation % | Ethane/Ethylene ($C_2/C_2^=$) Molar Ratio | Propane/Propylene ($C_3/C_3^=$) Molar Ratio | Benzene Purity % |
|---|---|---|---|---|---|---|
| 7 | Ni/W on ZSM-12/ Alumina | 40.0 | 92.5 | 93 | N/A | 100 |
| 8 | Fe on ZSM-12/ Alumina | 33.5 | 94.1 | 2 | 183 | 99.9 |
| 9 | Co/Mo on Meso-Mordenite/ Alumina | 58.0 | 98.8 | 5895 | N/A | 99.0 |

TABLE 5B

Performance Results - Conversion

| Example Number | Catalyst Descriptions | Benzene % | Toluene % | $C_9$ % | $C_{10}$ % | $C_9 + C_{10}$ % | Toluene + $C_9$ % | Toluene + $C_9 + C_{10}$ % | Actual Ring Loss % |
|---|---|---|---|---|---|---|---|---|---|
| 7 | Ni/W on ZSM-12/ Alumina | None | 32.7 | 58.7 | 52.5 | 57.1 | 46.6 | 47.5 | 1.2 |
| 8 | Fe on ZSM-11/ Alumina | None | 35.7 | 51.4 | 52.0 | 51.5 | 44.1 | 45.3 | 1.4 |
| 9 | Co/Mo on Meso-Mordenite/ Alumina | None | 28.1 | 58.6 | 74.6 | 62.8 | 44.2 | 48.9 | 1.7 |

TABLE 5C

Performance Results - Yields

| Example Number | Catalyst Descriptions | H2 Wt. % | Meth. Wt. % | Lt. Gas ($C_5^-$, incl. $C_1$) Wt. % | Non-Arom. Wt. % | BZ Wt. % | Tol. Wt. % | EB Wt. % | Xyls Wt. % | $C_9$ Arom. Wt. % |
|---|---|---|---|---|---|---|---|---|---|---|
| 7 | Ni/W on ZSM-12/ Alumina | −0.3 | 0 | 6.2 | 0.1 | 6.7 | 26.3 | 2.9 | 30.5 | 18.6 |
| 8 | Fe on ZSM-12/ Alumina | −0.2 | 0.1 | 4.3 | 0.1 | 6.0 | 25.1 | 3.4 | 28.1 | 21.9 |
| 9 | Co/Mo on Meso-Mordenite-Alumina | −0.5 | 0 | 8.2 | 0.3 | 7.0 | 28.4 | 2.5 | 31.2 | 18.3 |

| Example Number | Catalyst Descriptions | MEBZ Wt. % | TMB Wt. % | $C_{10}$ Arom. Wt. % | Di-EB Wt. % | DiM-EB Wt. % | TetraMBZ Wt. % | $C_{11}+$ Arom. Wt. % | Naphth. Wt. % | Approach Equil. Xylenes % |
|---|---|---|---|---|---|---|---|---|---|---|
| 7 | Ni/W on ZSM-12/ Alumina | 6.2 | 12.3 | 7.1 | 0.3 | 3.3 | 1.8 | 1.9 | 0.7 | 99.8 |
| 8 | Fe on ZSM-12/ Alumina | 6.4 | 13.9 | 7.1 | 0.4 | 4.2 | 2.1 | 3.7 | 0.9 | 94.1 |
| 9 | Co/Mo on Meso-Mordenite-Alumina | 5.1 | 13.1 | 3.9 | 0.2 | 2.0 | 1.5 | 0.7 | 0.1 | 98.0 |

The invention claimed is:

1. A catalyst composition comprising (i) a mordenite zeolite synthesized from TEA or MTEA, said mordenite zeolite having a mesopore surface area of greater than 30 m²/g and said mordenite zeolite comprising agglomerates composed of primary crystallites, wherein said primary crystallites have an average primary crystal size as measured by TEM of less than 80 nm and an aspect ratio of less than 2, (ii) 0.001 wt. % to 20.0 wt. % of at least one first metal comprising molybdenum or tungsten, based on the weight of the catalyst composition, and (iii) 0.001 wt. % to 20.0 wt. % of at least one second metal comprising cobalt or nickel, based on the weight of the catalyst composition, wherein said catalyst composition is treated with a source of sulfur in one or more steps at temperatures in a range of 204° C. (400° F.) up to about 480° C. (900° F.) or treated with a source of steam which comprises up to about 100% steam at temperatures in a range of about 260° C. (500° F.) to about 649° C. (1200° F.).

2. The catalyst composition of claim 1, wherein said source of sulfur is one or more of hydrogen sulfide, carbon disulfide and alkylsulfides which are selected from the group consisting of methylsulfide, dimethylsulfide, dimethyldisulfide, diethylsulfide and dibutyl sulfide, and mixtures of two or more thereof.

3. The catalyst composition of claim 1, further comprising at least one binder selected from the group consisting of alumina, silica, clay, titania, zirconia and a mixture of two or more thereof.

* * * * *